US011197815B2

(12) United States Patent
Parker et al.

(10) Patent No.: US 11,197,815 B2
(45) Date of Patent: Dec. 14, 2021

(54) PERSONAL CARE COMPOSITIONS

(71) Applicant: COLGATE-PALMOLIVE COMPANY, New York, NY (US)

(72) Inventors: Jodie Parker, Parsippany, NJ (US); Brajesh Jha, Midlothian, NJ (US); Emma Alvarado, Somerville, NJ (US)

(73) Assignee: Colgate-Palmolive Company, New York, NY (US)

( * ) Notice: Subject to any disclaimer, the term of this patent is extended or adjusted under 35 U.S.C. 154(b) by 329 days.

(21) Appl. No.: 16/314,522

(22) PCT Filed: Dec. 14, 2018

(86) PCT No.: PCT/US2018/065626
§ 371 (c)(1),
(2) Date: Dec. 31, 2018

(87) PCT Pub. No.: WO2020/122932
PCT Pub. Date: Jun. 18, 2020

(65) Prior Publication Data
US 2021/0220250 A1 Jul. 22, 2021

(51) Int. Cl.
*A61Q 19/10* (2006.01)
*A61K 8/81* (2006.01)
*A61K 8/36* (2006.01)
*A61K 8/37* (2006.01)
*A61K 8/60* (2006.01)

(52) U.S. Cl.
CPC ............ *A61K 8/8182* (2013.01); *A61K 8/361* (2013.01); *A61K 8/375* (2013.01); *A61K 8/602* (2013.01); *A61K 8/8158* (2013.01); *A61Q 19/10* (2013.01); *A61K 2800/30* (2013.01); *A61K 2800/5426* (2013.01)

(58) Field of Classification Search
CPC .... A61Q 19/10; A61K 8/375; A61K 2800/30; A61K 8/602; A61K 2800/5426; A61K 8/8158; A61K 2800/52; A61K 8/8182; A61K 8/37; A61K 8/361
USPC ...................................................... 424/78.02
See application file for complete search history.

(56) References Cited

U.S. PATENT DOCUMENTS

| | | | |
|---|---|---|---|
| 5,439,682 A | 8/1995 | Wivell et al. | |
| 6,428,799 B1 | 8/2002 | Cen et al. | |
| 2002/0006886 A1 | 1/2002 | Smith | |
| 2006/0008434 A1 | 1/2006 | Macchio | |
| 2008/0020057 A1 | 1/2008 | Lane | |
| 2011/0008267 A1 | 1/2011 | Arkin et al. | |
| 2011/0059038 A1 | 3/2011 | Gabelnick et al. | |
| 2015/0118177 A1 * | 4/2015 | Sartingen | A61K 8/342 424/78.02 |
| 2015/0297496 A1 * | 10/2015 | Kroon | A61K 8/8182 424/54 |
| 2017/0239155 A1 * | 8/2017 | Hartnett | A61K 8/368 |
| 2017/0326041 A1 * | 11/2017 | Tsuzuki | A61K 8/062 |

FOREIGN PATENT DOCUMENTS

| | | |
|---|---|---|
| DE | 102004027328 | 12/2005 |
| FR | 2966041 | 4/2012 |
| WO | 2007/127987 | 11/2007 |
| WO | 2014/165788 | 10/2014 |

OTHER PUBLICATIONS

Anonymous, 2005, "Shampoo—Formulierungen mit Konditionierefekten", Research Disclosure, Kenneth Mason Publications 497(13).
International Search Report and the Written Opinion of the International Searching Authority issued in International Application PCT/US2018/065626 dated Apr. 9, 2019.

* cited by examiner

Primary Examiner — Eisa B Elhilo

(57) ABSTRACT

Described herein are personal care compositions comprising a stability control system comprising a non-ionic opacifier, and a cationic polymer. Methods of making and using the compositions are also described.

20 Claims, No Drawings

PERSONAL CARE COMPOSITIONS

CROSS-REFERENCE TO RELATED APPLICATION

This application is a national stage entry under 35 U.S.C. § 371 of International patent Application No. PCT/US2018/65626, filed Dec. 14, 2018, the contents of which are hereby incorporated herein by reference in their entirety.

BACKGROUND

Personal care products, such as liquid hand soaps and body washes, may have appearances consumers typically associate with such products—such as milky-white liquids. While previous personal care products may include components that give the desired aesthetic appearance, such components may not be sustainable or permit the product to be prepared at ambient temperatures.

Removing certain components that have been traditionally used in personal care compositions presents challenges from a formulation stability perspective. As such, there is a need to identify sustainable ingredients that deliver the proper aesthetic, and also provide the requisite stability.

Embodiments of the present invention are designed to meet these, and other, needs.

BRIEF SUMMARY

Some embodiments of the present invention are directed to a personal care composition comprising: a base composition comprising water and at least one non-aqueous component; and a stability control system comprising a first component comprising a non-ionic opacifier; and a second component comprising an ionic polymer; wherein the first and second component are present in a weight ratio ranging from about 8:1 to about 1:4.

Other embodiments of the present invention include a personal care composition comprising: a base composition comprising water and at least one non-aqueous component; a stability control system comprising a first component comprising an ester-containing opacifier; and a second component comprising an ionic polymer; wherein the personal care composition is substantially free of styrene acrylate copolymer and the personal care composition is a soap.

Other embodiments of the present invention include a method of forming a personal care composition comprising: blending a stability control system with a base composition under ambient conditions; wherein the base composition comprises water and at least one non-aqueous component, and the stability control system comprises: a first component comprising an opacifier comprising a non-ionic compound; and a second component comprising an ionic polymer; and wherein the first and second component are present in a weight ratio ranging from about 8:1 to about 1:4.

In other embodiments, the present invention includes a stability control system comprising: water; a first component comprising a non-ionic opacifier; and a second component comprising an ionic polymer; wherein the first and second component are present in a weight ratio ranging from about 8:1 to about 1:4.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Unless otherwise specified, all percentages and amounts expressed herein and elsewhere in the specification should be understood to refer to percentages by weight. The amounts given are based on the active weight of the material. According to the present application, the term "about" means+/−5% of the reference value. According to the present application, the term "substantially free" less than about 0.01 wt. % based on the total of the referenced value.

It is contemplated that the invention described herein is not limited to the particular methodology, protocols, and reagents described as these may vary. It is also to be understood that the terminology used herein is for the purpose of describing particular embodiments only and is not intended to limit the scope of the present invention in any way.

Unless defined otherwise, all technical and scientific terms used herein have the same meanings as commonly understood by one of ordinary skill in the art to which this invention belongs. All patents, patent applications, publications, and other references cited or referred to herein are incorporated by reference for all purposes.

As used herein and in the appended claims, the singular forms "a", "an", and "the" include plural reference unless the context clearly dictates otherwise.

In some embodiments, the personal care composition may be a cosmetically acceptable composition which can be used for cleansing a skin surface. In other embodiments, the present invention relates to cosmetically acceptable compositions which can be used for cleansing a skin surface, especially a human skin surface, and which contain ingredients which are safe for the environment, i.e. ingredients which in sewage disposal plants are decomposed into substantially harmless substances, and which have a protective effect on the skin (e.g. against irritation and drying).

In some embodiments, the personal care composition may also provide an emollient effect, and which have excellent cosmetic and physical stability, and which are capable of leaving at least a part of the composition on the skin after rinsing. In some embodiments, the compositions of the present invention impart conditioning, smoothing and emollient properties to the skin and, thus, reduces the tendency to develop dry, irritated or otherwise traumatized skin.

The personal care composition of the present invention provides desired aesthetic properties indicative of the desired application while remaining surprisingly separation stable; and also having a suitable viscosity for the desired application. In a non-limiting example, the personal care composition may be a dispensable hand soap having the desired opaque aesthetic characteristics, whereby the hand soap not only exhibits a viscosity suitable for such dispensing but is also stable against phase separation.

Some embodiments of the present invention provide personal care compositions having a viscosity of from about 100 cps to about 15,000 cps—including all viscosities and sub-ranges there-between. In some embodiments, the performance of the stabilizing systems described herein are viscosity independent, i.e. the stabilizing systems are designed to prevent separation and provide the desired aesthetic regardless of the composition's viscosity.

As used herein, the term "skin surface" relates to the outermost surface of the body and embraces intact skin as well as injured skin surfaces, mucosa and mucous membranes. The term "skin surface" is used in a very broad sense embracing the epidermal layer of the skin and also the dermal layer of the skin. The epidermal layer of the skin is the outer (epithelial) layer and the deeper connective tissue layer of the skin is called the dermis. The skin may have a thick or a thin epidermis and is therefore often classified as thick or thin skin. In the present context, the term "skin" embraces thick skin as well as thin skin.

The term "soap" as used herein is given a broad meaning; and is intended to encompass agents to clean the hands and/or the body, including cosmetic or detergent substances as described in 21 C.F.R. 701.20, particularly products generally referred to as liquid hand soaps and body washes. Applicants recognize that, in some particular contexts, the term "soap" may be given a narrow definition as being a product primarily composed of alkali salts of fatty acids, but the term as used herein is not intended to be so limited. Thus, a liquid hand soap, for example, need not contain any alkali salts of fatty acids.

The personal care composition of the present invention may comprise a base composition and a stability control system that helps impart a surprising increase in separation stability. In some embodiments, the base composition may be present in an amount ranging from about 90 wt. % to about 99.5 wt. % based on the total weight of the personal care composition—including all amounts and sub-ranges there-between. In other embodiments, the base composition may be present in an amount ranging from about 95.0 wt. % to about 98 wt. % based on the total weight of the personal care composition—including all amounts and sub-ranges there-between.

The base composition may comprise water as well as non-aqueous components. Water may be present in the overall personal care composition in an amount ranging from about 50 to 95 wt. %, optionally 55% to about 90 wt. % to; further optionally about 60 wt. % to about 85 wt. %; still further optionally from about 65 wt. % to about 80 wt. %, including all amounts and sub-ranges there-between.

The personal care composition of the present invention may further comprise one or more additives such as an anti-microbial additive. Non-limiting examples of such additive include benzoic acid, benzoic acid salts, salicylic acid and salicylic salts, benzoic acid esters, sorbic acid, sorbic acid salts, sorbic acid esters, parabens, alkyl lactylate esters, citrate esters, alkyl malate esters, and alkyl glycolate esters, and mixtures of two or more said components. In a preferred embodiment, the anti-microbial additive comprises benzoic acid. The anti-microbial agent may be present in an amount ranging from about 0.1 wt. % to about 1 wt. % based on the total weight of the personal care composition—including all amounts and sub-ranges there-between.

The personal care composition may further comprise a pH modifier (also referred to as a pH adjusting agent). Non-limiting examples of such pH modifiers include acetic acid, adipic acid, ascorbic acid, citric acid, dehydroacetic acid, erythorbic acid, fumaric acid, glutaric acid, gluconic acid, hyaluronic acid, glycolic acid, lactic acid, malic acid, sorbic acid, succinic acid, tannic acid, tartaric acid, sulfuric acid, phosphoric acid, nitric acid, hydrochloric acid, sulfamic acid, carboxylic acid polymers, homo- or hetero-polymerized α-hydroxy carboxylic acids including poly lactic acid and poly lactic-glycolic acid and mixtures of two or more said acids.

The pH of the personal care composition may be adjusted using the pH modifier based on the desired end application of the personal care composition. For example, for hand soap applications, the personal care composition may comprise pH modifier in an amount such that the personal care composition has a pH value near the pH value of the skin (i.e. a pH about 5-5.5). In other embodiments, the personal care composition may have a higher pH than that of the skin to impart conditioning of the skin. In some embodiments, the suitable pH is from about 3.5 to about 5.5.

In a non-limiting embodiment, the pH modifier may be present in an amount ranging from about 0.1 wt. % to about 10 wt. % based on the total weight of the personal care composition—including all amounts and sub-ranges there-between.

The base composition may further comprise one or more surfactants. In some embodiments, the surfactant comprises cocamide MEA or an alkyl polyglucoside. In other embodiments, the surfactant may be anionic (e.g. sodium lauryl ether sulfate), cationic or non-ionic.

Amphoteric/zwitterionic surfactants may also be included in the composition. These surfactants are typically characterized by a combination of high surfactant activity, lather forming and mildness. Amphoteric surfactants include, but are not limited to, derivatives of aliphatic secondary and tertiary amines in which the aliphatic radical can be straight chain or branched and wherein one of the aliphatic substituents contains about 8 to about 18 carbon atoms and one contains an anionic water solubilizing group, e.g., carboxy, sulfonate, sulfate, phosphate, or phosphonate. Examples of such compounds include sodium 3-dodecyaminopropionate, sodium 3-dodecylaminopropane sulfonate, N-alkyl taurines and N-higher alkyl aspartic acids. Other equivalent amphoteric surfactants may be used. Examples of amphoteric surfactants include, but are not limited to, a range of betaines including, for example, high alkyl betaines, such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl)carboxymethyl betaine, oleyl dimethyl gamma-carboxypropyl betaine, and lauryl bis-(2-hydroxypropyl)alpha-carboxyethyl betaine, sulfobetaines such as coco dimethyl sulfopropyl betaine, stearyl dimethyl sulfopropyl betaine, amido betaines, amidosulfobetaines and the like. Betaines having a long chain alkyl group, particularly coco, may be particularly useful as are those that include an amido groups such as the cocamidopropyl and cocoamidoethyl betaines.

In certain embodiments, the compositions of the invention include one or more anionic surfactants. The anionic surfactants, which may be used in the compositions of the invention include water soluble anionic sulfonate surfactants and include sodium salts of linear $C_8$-$C_{16}$ alkyl benzene sulfonates; $C_{10}$-$C_{20}$ paraffin sulfonates, alpha olefin sulfonates containing about 10 to about 24 carbon atoms and $C_8$-$C_{18}$ alkyl sulfates and mixtures thereof.

The anionic surfactant may be any of the anionic surfactants known or previously used in the art of aqueous surfactant compositions. Suitable anionic surfactants include, but are not limited to, alkyl sulfates, alkyl ether sulfates, alkaryl sulfonates, alkyl succinates, alkyl sulfosuccinates, N-alkoyl sarcosinates, alkyl phosphates, alkyl ether phosphates, alkyl ether carboxylates, alkylamino acids, alkyl peptides, alkoyl taurates, carboxylic acids, acyl and alkyl glutamates, alkyl isethionates, and alpha-olefin sulfonates, especially their sodium, potassium, magnesium, ammonium and mono-, di- and triethanolamine salts. Preferred are sodium salts of the surfactants. The alkyl groups generally contain about 8 to about 18 carbon atoms and may be unsaturated.

In certain embodiments, suitable anionic surfactants include sodium lauryl ether sulfate, ammonium lauryl ether sulfate, sodium lauryl sulfate, ammonium lauryl sulfate, triethanolamine lauryl sulfate, disodium laureth sulfosuccinate, sodium cocoyl isethionate, sodium $C_{12}$-$C_{14}$ olefin sulfonate, sodium laureth-6 carboxylate, sodium $C_{12}$-$C_{15}$ pareth sulfate, sodium methyl cocoyl taurate, sodium dodecylbenzene sulfonate, sodium cocoyl sarcosinate, triethanolamine monolauryl phosphate, and fatty acid soaps. Preferred are sodium lauryl ether sulfate, sodium lauryl sulfate, disodium laureth sulfosuccinate, sodium cocoyl isethionate, sodium $C_{12}$-$C_{14}$ olefin sulfonate, sodium laureth-6 carboxylate, sodium $C_{12}$-$C_{15}$ pareth sulfate, sodium methyl cocoyl taurate, sodium dodecylbenzene sulfonate, and sodium cocoyl sarcosinate.

In certain illustrative embodiments, examples of suitable sulfonated anionic surfactants include, but are not limited to, alkyl mononuclear aromatic sulfonates, such as the higher alkylbenzene sulfonates containing in one embodiment 8 to 18 carbon atoms, in another embodiment 11 to 16 carbon atoms, and in another embodiment 14 or 15 carbon atoms, the higher alkyl group in a straight or branched chain, or C8-15 alkyl toluene sulfonates and C8-C15 alkyl phenol sulfonates. In another embodiment, the alkylbenzene sulfonate is a linear alkylbenzene sulfonate having a higher content of 3-phenyl (or higher) isomers and a correspondingly lower content (well below 50%) of 2-phenyl (or lower) isomers, such as those sulfonates wherein the benzene ring is attached mostly at the 3 or higher (for example 4, 5, 6 or 7) position of the alkyl group and the content of the isomers in which the benzene ring is attached in the 2 or 1 position is correspondingly low. Illustrative materials are described in U.S. Pat. No. 3,320,174. Of these, preferred are sodium salts of the anionic surfactants.

In another embodiment, examples of suitable sulfonated anionic surfactants include, but are not limited to, those surface-active or detergent compounds, which contain an organic hydrophobic group containing generally about 8 to about 26 carbon atoms or 10 to 18 carbon atoms in their molecular structure and at least one water-solubilizing group including, but not limited to, sulfonate, sulfate and carboxylate so as to form a water-soluble detergent. Usually, the hydrophobic group will include a $C_8$-$C_{22}$ alkyl, alkyl or acyl group. Such surfactants are employed in the form of water-soluble salts and the salt-forming cation is sodium, potassium, ammonium, magnesium and mono-, di- or tri-$C_2$-$C_3$ alkanolammonium. In an illustrative embodiment the cations are sodium, magnesium or ammonium cations, and preferred is sodium.

Other suitable anionic surfactants encompassed within the scope of the invention include, but are not limited to, the olefin sulfonates, including long-chain alkene sulfonates, long-chain hydroxyalkane sulfonates or mixtures of alkene sulfonates and hydroxyalkane sulfonates. These olefin sulfonate detergents may be prepared in a known manner by the reaction of sulfur trioxide ($SO_3$) with long-chain olefins containing 8 to 25, or 12 to 21 carbon atoms and having the formula $RCH=CHR_1$ where R is a higher alkyl group of 6 to 23 carbons and R1 is an alkyl group of 1 to 17 carbons or hydrogen to form a mixture of sulfones and alkene sulfonic acids which is then treated to convert the sulfones to sulfonates. In other embodiments olefin sulfonates contain about 14 to about 16 carbon atoms in the R alkyl group and are obtained by sulfonating an alpha-olefin.

Other examples of suitable anionic sulfonate surfactants encompassed within the scope of the invention include the paraffin sulfonates containing about 10 to about 20, or about 13 to about 17 carbon atoms.

In a non-limiting embodiment, the surfactant may be an alkyl polyglycosides having the formula (I)

$$R-O-Z_n \qquad (I)$$

in which R represents a linear or branched, saturated or unsaturated aliphatic alkylradical having 7 to 18 carbon atoms or mixtures thereof, $Z_n$ represents a polyglycosyl radical or a mixture of polyglycosyl radicals, wherein $Z_n$ has an average value of from 1.0 to 3.0 hexose or pentose units for the total shorter-chain alkyl polyglycosides of formula (I) in the composition. Preference is given to alkyl polyglycosides having alkyl radicals of 8 to 16 carbon atoms.

The polyglycosyl radicals $Z_n$ may be determined by the selection of the carbohydrate and/or the desired average degree of polymerization n. In a non-limiting example, carbohydrates such as starch, maltodextrins, dextrose, galactose, mannose, xylose and the like, can be used. Carbohydrates which are available on a large scale are preferred; for example, starch, maltodextrins, and, in particular, dextrose.

In some embodiments, the surfactant system comprises a blend of Sodium Laureth Sulfate and Cocamide MEA; cocamidopropyl betaine and a C12-14 Alcohol EO 2:1 NA Sulfate. In some embodiments, the surfactant system comprises from about 5 wt. % to about 30 wt. % of the personal care composition. In some embodiments, the surfactant system comprises from about 10 wt. % to about 25 wt. % of the personal care composition. In some embodiments, the surfactant system comprises from about 15 wt. % to about 20 wt. % of the personal care composition.

In a non-limiting embodiment, the surfactant may be present in an amount ranging from about 5 wt. % to about 15 wt. % based on the total weight of the personal care composition—including all amounts and sub-ranges therebetween. In a preferred embodiment, the surfactant may be present in an amount ranging from about 8 wt. % to about 12 wt. % based on the total weight of the personal care composition—including all amounts and sub-ranges therebetween.

Some embodiments provide a personal care composition comprising a surfactant system. In some embodiments, the surfactant system comprises an anionic surfactant; a non-ionic surfactant and/or an amphoteric surfactant. In some embodiments, the surfactant system comprises an anionic surfactant (e.g. sodium laureth sulfate); a non-ionic surfactant (e.g. C12-14 Alcohol EO 2:1 NA Sulfate) and an amphoteric surfactant (e.g. cocamidopropyl betaine).

In some embodiments, the personal care composition may comprise suitable antioxidants; that is, substances known to inhibit oxidation. Antioxidants suitable for use in accordance with the present invention include, but are not limited to, butylated hydroxytoluene, ascorbic acid, sodium ascorbate, calcium ascorbate, ascorbic palmitate, butylated hydroxyanisole, 2,4,5-trihydroxybutyrophenone, 4-hydroxymethyl-2,6-di-fert-butylphenol, erythorbic acid, gum guaiac, propyl gallate, thiodipropionic acid, dilauryl thiodipropionate, tert-butylhydroquinone and tocopherots such as vitamin E, and the like, including pharmaceutically acceptable salts and esters of these compounds; e.g., butylated hydroxytoluene, butylated hydroxyanisole, propyl gallate, ascorbic acid, pharmaceutically acceptable salts or esters thereof, or mixtures thereof; for example butylated hydroxytoluene. When the personal care compositions of the present invention contain at least one antioxidant, the total amount of antioxidant present may be from about 0.001 to 0.5 wt %, 0.05 to 0.5 wt %, e.g. about 0.1%.

In other embodiments, the personal care compositions may also comprise suitable preservatives. Preservatives are compounds added to a formulation to act as an antimicrobial agent. Among preservatives known in the art as being effective and acceptable parenteral formulations are benzalkonium chloride, benzethonium, chlorohexidine, phenol, m-cresol, benzyl alcohol, methylparaben, propylparaben, chlorobutanol, o-cresol, p-cresol, chlorocresol, phenylmercuric nitrate, thimerosal, benzoic acid, sodium benzoate, sodium salicylate and various mixtures thereof. When the compositions contain at least one preservative, the total amount of preservative present is from about 0.01 to about 1 wt %, depending on the characteristics of the particular preservatives selected and the amount required for effective preservation in the particular formulation. In some embodiments, the compositions comprise sodium benzoate and sodium salicylate in a total amount of 0.1% to 1%.

Still further embodiments provide personal care compositions comprising a chelating agent that forms complexes with metal cations that do not cross a lipid bilayer. Examples of suitable chelating agents include ethylene diamine tetraacetic acid (EDTA), ethylene glycol-bis(beta-aminoethyl ether)-N,N,N',N'-tetraacetic acid (EGTA) and 8-Amino-2-[(2-amino-5-methylphenoxy)methyl]-6-methoxyquinoline-N5N,N',N'-tetraacetic acid, tetrapotassium salt (QUIN-2). When the compositions contain at least one chelating agent, the total amount of chelating agent present is 0.005 to 2 weight % by weight, depending on the particular chelator and formulation selected. For example, in some embodiments, the compositions may contain 0.01 to 0.3 weight % of tetrasodium EDTA. In other embodiments, the compositions may be free of tetrasodium EDTA.

The stability control system of the personal care composition may comprise a first component and a second component. The first component may comprise an opacifier. The second component may comprise an ionic polymer.

The stability control system may be present in an amount ranging from about 0.05 wt. % to about 4.0 wt. % based on the total weight of the personal care composition—including all amounts and sub-ranges there-between. In a preferred embodiment, the stability control system may be present in an amount ranging from about 0.1 wt. % to about 3.5 wt. % based on the total weight of the personal care composition—including all amounts and sub-ranges there-between.

In some embodiments, the stability control system comprises an opacifier. In some embodiments, the opacifier is a non-ionic opacifier. In some embodiments, the non-ionic opacifier comprises a wax dispersion. In some embodiments the wax dispersion comprises one or more of glycol distearate, coco-glucoside, glyceryl oleate, glyceryl stearate. In certain embodiments, the wax dispersion comprises water, benzoic acid, citric acid, coco-glucoside, glyceryl oleate, glyceryl stearate and glyceryl distearate.

In other embodiments, the opacifier may comprise one or more of glycol stearate, cocamidopropyl betaine, and laureth-4. In other embodiments, the opacifier may comprise one or more of cetyl palmitate glyceryl stearate and hydrogenate castor oil.

In some embodiments, the stability control system is substantially free of styrene acrylate copolymer. In other embodiments, the stability control system is free of styrene acrylate copolymer. In further embodiments, the stability control system is substantially free of styrene, or a derivative thereof. Still further embodiments provide stability control systems that are fee of styrene, or a derivative thereof.

In some embodiments, the stability control system comprises a first component and a second component. In some embodiments, the first component may be present in an amount ranging from about 0.2 wt. % to about 2.5 wt. % based on the total weight of the personal care composition—including all amounts and sub-ranges there-between. In some embodiments, the first component may be present in an amount ranging from about 0.25 wt. % to about 2.1 wt. % based on the total weight of the personal care composition—including all amounts and sub-ranges there-between.

The first component may have an acidic pH. The first component may have a pH ranging from about 3 to about 5—including all pH values and sub-ranges there-between. In some embodiments, the first component may have a pH ranging from about 3 to about 4—including all pH values and sub-ranges there-between.

In some embodiments, the second component may be ionic. In some embodiments, the second component may comprise an ionic polymer. In other embodiments, the ionic polymer may be a cationic polymer. Non-limiting examples of cationic polymer include copolymer of acrylamide and a diallyl dimethylammonium salt. A non-limiting example of the diallyl dimethylammonium salt is diallyl dimethylammonium chloride.

In some embodiments, the second component may be substantially free of styrene acrylate copolymer. In some embodiments, the second component may be substantially free of styrene.

In some embodiments, the second component may be present in an amount ranging from about 0.1 wt. % to about 1.5 wt. % based on the total weight of the personal care composition—including all amounts and sub-ranges there-between. The second component may be present in an amount ranging from about 0.1 wt. % to about 1.2 wt. % based on the total weight of the personal care composition—including all amounts and sub-ranges there-between.

In some embodiments, the first component and the second component may be present in amounts resulting in a weight ratio ranging from about 8:1 to about 1:4—including all ratios and sub-ranges there-between. In other embodiments, the first component and the second component may be present in amounts resulting in a weight ratio ranging from about 7:1 to about 1:4—including all ratios and sub-ranges there-between. The first component and the second component may be present in amounts resulting in a weight ratio ranging from about 6:1 to about 1:4—including all ratios and sub-ranges there-between. The first component and the second component may be present in amounts resulting in a weight ratio ranging from about 5:1 to about 1:4—including all ratios and sub-ranges there-between. The first component and the second component may be present in amounts resulting in a weight ratio ranging from about 4:1 to about 1:4—including all ratios and sub-ranges there-between. The first component and the second component may be present in amounts resulting in a weight ratio ranging from about 4:1 to about 1:3.6—including all ratios and sub-ranges there-between. The first component and the second component may be present in amounts resulting in a weight ratio ranging from about 4:1 to about 1:3.6—including all ratios and sub-ranges there-between.

The first component and the second component may be present in amounts resulting in a weight ratio ranging from about 8:1 to about 1.1:1—including all ratios and sub-ranges there-between. The first component and the second component may be present in amounts resulting in a weight ratio ranging from about 7:1 to about 1.1:1—including all ratios and sub-ranges there-between. The first component and the second component may be present in amounts resulting in a weight ratio ranging from about 6:1 to about 1.1:1—including all ratios and sub-ranges there-between. The first component and the second component may be present in amounts resulting in a weight ratio ranging from about 5:1 to about 1.1:1—including all ratios and sub-ranges there-between. The first component and the second component may be present in amounts resulting in a weight ratio ranging from about 4:1 to about 1.1:1—including all ratios and sub-ranges there-between.

In some embodiments, the first component and the second component may be present in amounts resulting in a weight ratio ranging from about 2.8:1 to about 1:1.8—including all ratios and sub-ranges there-between. In some embodiments, the first component and the second component may be present in amounts resulting in a weight ratio ranging from about 1:1 to about 5:1—including all ratios and sub-ranges there-between.

Non-limiting optional benefit components include humectants and solutes. A variety of humectants and solutes can be employed and can be present at a level of from about 0.1% to about 50%, preferably from about 0.5% to about 35%, and more preferably from about 2% to about 20%, by weight of the mild body wash composition. A preferred humectant is glycerin. A preferred water soluble, organic material is selected from the group consisting of a polyol of the structure:

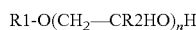

where R1=H, C1-C4 alkyl; R2=H, $CH_3$ and n=1-200; C2-C10 alkane diols; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerol, hexanetriol, propylene glycol, hexylene glycol and the like; polyethylene glycol; sugars and starches; sugar and starch derivatives (e.g. alkoxylated glucose); panthenol (including D-, L-, and the D,L-forms); pyrrolidone carboxylic acid; hyaluronic acid; lactamide monoethanolamine; acetamide monoethanolamine; urea; and mixtures thereof. The most preferred polyols are selected from the group consisting of glycerine, polyoxypropylene(1)glycerol and polyoxypropylene(3)glycerol, sorbitol, butylene glycol, propylene glycol, sucrose, urea and triethanol amine.

Nonionic polyethylene/polypropylene glycol polymers are preferably used as skin conditioning agents. Polymers useful herein that are especially preferred are PEG-2M wherein x equals 2 and n has an average value of about 2,000 (PEG 2-M is also known as Polyox WSR® N-10 from Union Carbide and as PEG-2,000); PEG-5M wherein x equals 2 and n has an average value of about 5,000 (PEG 5-M is also known as Polyox WSR® 35 and Polyox WSR® N-80, both from Union Carbide and as PEG-5,000 and Polyethylene Glycol 200,000); PEG-7M wherein x equals 2 and n has an average value of about 7,000 (PEG 7-M is also known as Polyox WSR® (N-750 from Union Carbide); PEG-9M wherein x equals 2 and n has an average value of about 9,000 (PEG 9-M is also known as Polyox WSR® N-3333 from Union Carbide); PEG-14 M wherein x equals 2 and n has an average value of about 14,000 (PEG 14-M is also known as Polyox WSR-205 and Polyox WSR® N-3000 both from Union Carbide); and PEG-90M wherein x equals 2 and n has an average value of about 90,000. (PEG-90M is also known as Polyox WSR®-301 from Union Carbide.)

Other non-limiting examples of these optional benefit components include vitamins and derivatives thereof (e.g., ascorbic acid, vitamin E, tocopheryl acetate, and the like); sunscreens; thickening agents (e.g., polyol alkoxy ester, available as Crothix from Croda); anti-acne medicaments (resorcinol, salicylic acid, and the like); skin soothing and healing agents such as aloe vera extract, allantoin and the like; chelators and sequestrants; and agents suitable for aesthetic purposes such as fragrances, essential oils, skin sensates, pigments, lakes, colorings, and the like (e.g., clove oil, menthol, camphor, *eucalyptus* oil, and eugenol).

In some embodiments, the personal care compositions can comprise a particle. Water insoluble solid particle of various shapes and densities is useful. In a preferred embodiment, the particle tends to have a spherical, an oval, an irregular, or any other shape in which the ratio of the largest dimension to the smallest dimension (defined as the Aspect Ratio) is less than about 10. More preferably, the Aspect Ratio of the particle is less than about 8, still more preferably the Aspect Ratio of the particle is less than about 5.

In some embodiments, the particle has a particle size of less than about 100 μm, preferably less than about 80 μm, and more preferably the particle size of less than about 60 μm. In some embodiments, the particle of the present invention preferably has a particle size of greater than about 0.1 μm, preferably a particle size of greater than about 0.5 μm, more preferably, a particle size greater than about 1 μm, still more preferably a particle size greater than about 2 μm, even more preferably a particle size greater than about 3 μm, and still even more preferably a particle size greater than about 4 μm.

In other embodiments, the particle has a diameter from about 1 μm to about 70 μm, or from about 2 μm to about 65 μm, and even from about 2 μm to about 60 μm in diameter.

In some embodiments, the personal care composition comprises the particle at a cosmetically efficacious level. Preferably, the particles are present from at least about 0.1% by weight of the composition, more preferably at least about 0.2% by weight of composition, even more preferably at least about 0.5%, still more preferably at least about 1%, and even still more preferably at least 2% by weight of composition. In the mild body wash composition of the present invention, preferably the particles comprise no more than about 50% by weight of composition, more preferably no more than about 30%, still more preferably no more than about 20%, and even more preferably no more than about 10% by weight of composition.

Preferably, the particle will also have physical properties which are not significantly affected by typical processing of the composition. Preferably, a particle having a melting point greater than about 70° C. is used, more preferably having a melting point greater than about 80° C., and even more preferably having a melting point of greater than about 95° C. is used. As used herein, melting point would refer to the temperature at which the particle transitions to a liquid or fluid state or undergoes significant deformation or physical property changes. In addition, many of the particles of present invention are cross-linked or have a cross-linked surface membrane. These particles do not exhibit a distinct melting point. Cross-linked particles are also useful as long as they are stable under the processing and storage conditions used in the making of compositions.

The particles that can be present in the present invention can be natural, synthetic, or semi-synthetic. In addition, hybrid particles can also be present. Synthetic particles can made of either cross-linked or non cross-linked polymers. The particles of the present invention can have surface charges or their surface can be modified with organic or inorganic materials such as surfactants, polymers, and inorganic materials. Particle complexes can be present.

Nonlimiting examples of synthetic particles include nylon, silicone resins, poly(meth)acrylates, polyethylene, polyester, polypropylene, polystyrene, polyurethane, polyamide, epoxy resins, urea resins, and acrylic powders. Non limiting examples of useful particles are Microease 110S, 114S, 116 (micronized synthetic waxes), Micropoly 210, 250S (micronized polyethylene), Microslip (micronized polytetrafluoroethylene), and Microsilk (combination of polyethylene and polytetrafluoroethylene), all of which are available from Micro Powder, Inc. Additional examples include Luna (smooth silica particles) particles available from Phenomenex, MP-2200 (polymethylmethacrylate), EA-209 (ethylene/acrylate copolymer), SP-501 (nylon-12), ES-830 (polymethly methacrylate), BPD-800, BPD-500 (polyurethane) particles available from Kobo Products, Inc. and silicone resins sold under the name Tospearl particles by GE Silicones. Ganzpearl GS-0605 crosslinked polystyrene (available from Presperse) is also useful.

Non-limiting examples of hybrid particles include Ganzpearl GSC-30SR (Sericite & crosslinked polystyrene hybrid powder), and SM-1000, SM-200 (mica and silica hybrid powder available from Presperse).

In some embodiments, the particle is an exfoliant particle selected from the group consisting of polyethylene, microcryatalline wax, jojoba esters, amourphors silica, talc, tracalcium orthophosphate, or blends thereof, and the like. The exfoliant particle has a particle size dimension along the major axis of the particle of from about 100 microns to about 600 microns, preferably from about 100 microns to about 300 microns. The exfoliant particle has a hardness of less than about 4 Mohs, preferably less than about 3 Mohs. The hardness as so measured is a criterion of the resistance of a particular material to crushing. It is known as being a fairly good indication of the abrasive character of a particulate ingredient. Examples of materials arranged in increasing order of hardness according to the Moh scale are as follows: h(hardness)-1:talc; h-2: gypsum, rock salt, crystalline salt in general, barytes, chalk, brimstone; h-4: fluorite, soft phosphate, magnesite, limestone; h-5: apatite, hard phosphate, hard limestone, chromite, bauxite; h-6: feldspar, ilmenite, hornblendes; h-7: quartz, granite; h-8: topaz; h-9: corrundum, emery; and h-10: diamond.

Preferably, the exfoliant particle has a color distinct from the cleansing base. The exfoliant particle is preferably present at a level of less than about 10%, preferably less than about 5%, by wt of the composition.

In some embodiments, the particle is a shiny particle. Nonlimiting examples of shiny particles include the following: interference pigment, multi-layered pigment, metallic particle, solid and liquid crystals, or combinations thereof.

It has been surprisingly discovered that the combination of the first component with the second component provides an unexpected improvement in separation stability for personal care products. Specifically, for personal care products comprising a base composition, the addition of the stability control system allows for the personal care product to maintain the desired opaque aesthetic properties of the personal care composition while achieving superior separation-stability for composition that are substantially free of styrene. In some embodiments, the personal care compositions of the present invention are completely free of styrene.

Embodiments of the invention will be described in greater detail by way of specific examples. The following examples are offered for illustrative purposes and are not intended to limit the invention in any manner. While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

EXAMPLES

Example 1

An experiment was performed to evaluate the separation stability of a styrene-containing control composition (Control 1); a personal care composition according to some embodiments of the present invention comprising—in relevant part—a cationic polymer and a wax dispersion (Ex. I); and a comparative composition (Comp. Ex. I). A more detailed description of these formulas is provided in Table 1 (below). Stability was evaluated by an ability to prevent visually perceivable phase separation at a temperature of 49° C., for four (4) weeks. Compositions that were able to avoid visually perceivable phase separation after four weeks at 49° C., demonstrated adequate stability.

TABLE 1

| Ingredient | Control 1 | Ex. I Wt. % | Comp. Ex. I |
|---|---|---|---|
| Water | QS | QS | QS |
| Surfactant System | 20.24 | 20.32 | 20.24 |
| Cationic polymer | — | 0.50 | — |
| Humectant | 0.01 | 0.01 | 0.01 |
| Styrene/Acrylates Copolymer | 0.50 | — | — |
| Salt | 0.50 | 0.50 | 0.50 |
| Chelating agent(s) | 0.20 | 0.20 | 0.20 |
| pH modifier | 2.25 | 2.25 | 2.25 |
| Preservative | 0.60 | 0.60 | 0.60 |
| Pearlizer | 1.50 | — | 1.50 |
| Fragrance | 0.45 | — | 0.45 |
| Wax Dispersion | — | 2.00 | 2.00 |
| Total | 100 | 100 | 100 |
| Phase Separation | No | No | Yes |

As illustrated by the results described in Table 1 (above) an exemplary composition of the present invention demonstrated separation stability, while the comparative formula that did not include the inventive combination of the present invention had visually perceivable signs of separation.

Example 2

Two reference compositions containing styrene (Control 2 and Control 3); two comparative compositions (Comp. Ex. II and Comp. Ex. III) and two exemplary compositions of the present invention (Ex. II and Ex. III) were evaluated to assess the impact of pH, viscosity, surfactant type and surfactant concentration on phase separation. Similar to the method described in Example 1 (above), the compositions were exposed to a temperature of 49° C., for four (4) weeks to evaluate their stability. The formulas are described below in Table 2.

TABLE 2

| Ingredients | Control 2 | Control 3 | Comp. Ex. II | Comp. Ex. III | Ex. II | Ex. III |
|---|---|---|---|---|---|---|
| | | | Wt. % | | | |
| Water | 68.6 | 72.22 | 67.2 | 71.945 | 67.2 | 71.945 |
| Surfactant System | 18.8 | 18.3 | 18.8 | 18.3 | 18.8 | 18.3 |
| Cationic Polymer | — | — | — | — | 0.5 | 0.1 |
| Humectant(s) | 7.45 | 5 | 7.45 | 5 | 7.45 | 5 |
| Preservative(s) | 0.6 | 0.6 | 0.6 | 0.6 | 0.6 | 0.6 |
| Emollient(s) | 0.5 | — | 0.5 | — | 0.5 | — |
| pH Modifier(s) | 1.15 | 1.1 | 1.15 | 1.1 | 1.15 | 1.1 |
| Fragrance | 0.5 | 0.5 | 0.5 | 0.5 | 0.5 | 0.5 |
| Salt | 0.5 | 0.98 | 0.5 | 0.98 | 0.5 | 0.98 |
| Metal ion source | 0.1 | — | 0.1 | — | 0.1 | — |
| Moisturizer(s) | 1.2 | 1.2 | 1.2 | 1.2 | 1.2 | 1.2 |
| Styrene/Acrylates Copolymer | 0.6 | 0.1 | — | — | — | — |
| Wax Dispersion | — | — | 1.5 | 0.275 | 1.5 | 0.275 |
| Total | 100 | 100 | 100 | 100 | 100 | 100 |
| Phase Separation | No | No | Yes | Yes | No | No |

The results described in Table 2 (above) demonstrate that pH, viscosity, surfactant type and surfactant concentration were not the driving force in achieving separation stability. Rather, the combination of a cationic polymer and a wax dispersion (Ex. II and Ex. III) provided the necessary stability in a styrene-free formula.

Example 3

Additional experiments were conducted to confirm the stability benefit provided by the stabilizer system of the present invention. The formulas tested, and results from these experiments, are described in Table 3 (below).

TABLE 3

| Ingredient | Control 4 | Control 5 | Ex. IV | Ex. V | Comp. Ex. IV | Comp. Ex. V |
|---|---|---|---|---|---|---|
| | | | Wt. % | | | |
| Water | 71.80 | 79.18 | 70.80 | 77.68 | 71.80 | 77.68 |
| Surfactant System | 20.14 | 14.75 | 20.14 | 14.75 | 20.14 | 14.75 |
| Cationic Polymer | 3.125 | 2.50 | 3.125 | 2.50 | — | — |
| Humectant(s) | 1.20 | — | 1.20 | — | 1.20 | — |
| Minors (e.g. Fragrance and Colorants) | ~1.00 | ~0.35 | ~1.00 | ~0.35 | ~1.00 | ~0.35 |
| Styrene/Acrylates Copolymer | 0.95 | 0.50 | — | — | — | — |
| Salt(s) | 0.70 | 1.50 | 0.70 | 1.50 | 0.70 | 1.50 |
| Chelating Agent(s) | 0.25 | 0.25 | 0.25 | 0.25 | 0.25 | 0.25 |
| Preservative(s) | 0.54 | 0.56 | 0.54 | 0.56 | 0.54 | 0.56 |
| pH Modifier(s) | 0.22 | 0.16 | 0.22 | 0.16 | 0.22 | 0.16 |
| Pearlizing Agent(s) | 0.050 | — | — | — | — | — |
| Wax Dispersion | — | — | 2.00 | 2.00 | 2.00 | 2.00 |
| Total | 100 | 100 | 100 | 100 | 100 | 100 |
| Phase Separation | No | No | No | No | Yes | Yes |

Similar to the results observed above in Examples 1 and 2, the data described in Table 3 (above) confirm that the inventive stabilizing system of the present invention is responsible for preventing the visually perceivable phase separation observed in styrene-free compositions, which do not include the inventive stabilizing system of the present invention (Comp. Ex. IV and Comp. Ex. V).

Example 4

A backbone formulation was prepared to evaluate the opacifying effect of various ingredients and ingredient combinations. The backbone is described below in Table 4.

TABLE 4

| Ingredient | Wt. % |
|---|---|
| Water | 65-80 |
| Surfactant System | 3-30 |
| Humectant(s) | 0.01-10 |
| Salt(s) | 0-2 |
| Preservative(s) | 0.1-1 |
| Chelating Agent(s) | 0.1-0.5 |
| pH Modifier(s) | 0.1-0.3 |

Several compositions were tested to determine—inter alia—the temperature at which they provide a homogenous opaque appearance. This experiment tested various opacifier combinations; specifically, those described in Table 5 (below).

TABLE 5

| Ingredient | A | B | C | D | E | F | G | H | I | J |
|---|---|---|---|---|---|---|---|---|---|---|
| | | | | | Wt. % | | | | | |
| Glycol Stearate | 100 | | 100 | | | | | | | |
| Fatty acids, C16-18, ester | | 96 | | 20 | | | | | | |
| Ethylene glycol | | | 4 | | | | | | | |
| Water | | | | 62 | 51.1 | 45 | 56.5 | 58 | | 60 |
| Glycol distearate | | | | 15 | | | | | | |
| Cocamide MEA | | | | 7.5 | | | | | | |
| Sodium Laureth Sulfate | | | | 13 | | | | | | 12 |
| Laureth-10 | | | | 2.5 | | | | | | |
| CAP-Betaine | | | | | 7.5 | 7.5 | | | | |
| Formic acid | | | | | 0.3 | | | | | |
| C12-14 Ethoxylated Alcohol | | | | | 20 | | | | | |
| Sodium chloride | | | | | 1.1 | | | | | |
| Laureth-4 | | | | | | 7.5 | | | | |
| Glycol distearate | | | | | | 40 | | | | |
| Fatty acids, C16-18, C12-1 | | | | | | | 30 | 25 | | |
| Hydrogenated Castor Oil | | | | | | | 3 | | | |
| Glycerides, C14-18 mono- a | | | | | | | 3 | 3 | | |
| Beheneth | | | | | | | 7.5 | | | |
| Benzoic acid | | | | | | | | 0.5 | | |
| Citric acid | | | | | | | | 0.5 | | |
| Decylglucoside | | | | | | | | 10 | | |
| Glyceryl Oleate | | | | | | | | 3 | | |
| Distearyl Ether | | | | | | | | | 100 | 10 |
| Dicaprylyl Ether | | | | | | | | | | 3 |
| Polyethylene glycol distearate | | | | | | | | | | 15 |

Each formulation was blended and observed for proper mixing; and to determine whether a styrene-free formula could be prepared at ambient temperature and also provide the proper aesthetic (i.e. white). The results are set forth below in Table 6.

TABLE 6

| Endpoint | A | B | C | D | E | F | G | H | I | J |
|---|---|---|---|---|---|---|---|---|---|---|
| Pearl/White | White | White | White | Pearl | Pearl | Pearl | Pearl | White | White | White |
| Opaque at Low Blending Temp | | | | | | | | X | | X |
| Opaque but Required High Blending Temp | X | X | X | | | | | | X | |

As illustrated by the results described in Table 6 (above), opacifier H was styrene-free and able to provide an opaque aesthetic in a personal care composition prepared at ambient temperature.

Example 5

Several personal care compositions were formulated using the backbone formulation described in Table 4 (above), and a combination of a wax dispersion (e.g. Formula H in Table 5 (above)) and a cationic polymer (see, Table 7 (below)). In accordance with the methods described in Examples 1 and 2, the stability of the compositions was evaluated to determine the optimal concentrations of the wax dispersion and cationic polymer.

TABLE 7

| | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| | | | | | Wt. % | | | | |
| Backbone | 99.725 | 99.625 | 99.475 | 99.225 | 98.725 | 98.0 | 97.75 | 97.5 | 97.0 |
| Wax Dispersion | 0.275 | 0.275 | 0.275 | 0.275 | 0.275 | 2.0 | 2.0 | 2.0 | 2.0 |
| Cationic Polymer | — | 0.1 | 0.25 | 0.5 | 1.0 | — | 0.25 | 0.5 | 1.0 |
| Wax Dispersion:Cationic Polymer Ratio | — | 2.75:1 | 1.1:1 | 1:1.8 | 1:3.6 | — | 8:1 | 4:1 | 2:1 |
| Phase Separation | Yes | No | No | No | No | Yes | Yes | No | No |

As demonstrated by the results described in Table 7 (above), a combination of a wax dispersion and a cationic polymer in a weight ratio ranging from about 1:4 to about less than 8:1 created a separation stable personal care composition, while phase separation was observed with compositions having a weight ratio of a wax dispersion: cationic polymer outside of this range.

Example 6

Colorimetry readings of three (3) personal care compositions formulated using the backbone formulation described in Table 4 (above), and a combination of a wax dispersion (e.g. Formula H in Table 5 (above)) and a cationic polymer, and one comparative composition were taken with a X-Rite Colorimeter after 4 weeks at 49° C. The results are described below in Table 8, using an unaged composition having a L*=63.42, as the reference product.

TABLE 8

|  | Comp. Ex. VI | Ex. 11 Wt. % | Ex. 12 | Ex. 13 |
|---|---|---|---|---|
| Backbone | 98.0 | 97.9 | 97.75 | 97.5 |
| Wax Dispersion | 2.0 | 2.0 | 2.0 | 2.0 |
| Cationic Polymer | — | 0.1 | 0.25 | 0.5 |
| ΔL | −38.40 | −10.48 | −9.04 | −6.72 |

The results described in Table 8 (above) demonstrate that the inventive combination of a wax dispersion and a cationic polymer protects the composition from color degradation, even under accelerated aging conditions.

Example 7

Colorimetry readings of three (3) additional personal care compositions formulated using the backbone formulation described in Table 4 (above), and a combination of a wax dispersion (e.g. Formula H in Table 5 (above)) and a cationic polymer, and another comparative composition were taken with a X-Rite Colorimeter after 4 weeks at 49° C. The results are described below in Table 9, using an unaged composition having a L*=46.48, as the reference product. ΔL against the referenced product, are reported for the comparative example and the three exemplary compositions of the present invention.

TABLE 9

|  | Comp. Ex. VII | Ex. 14 Wt. % | Ex. 15 | Ex. 16 |
|---|---|---|---|---|
| Backbone | 99.725 | 99.625 | 99.475 | 99.225 |
| Wax Dispersion | 0.275 | 0.275 | 0.275 | 0.275 |
| Cationic Polymer | — | 0.1 | 0.25 | 0.5 |
| ΔL | +4.17 | −10.48 | −9.04 | −6.72 |

The results described in Table 9 (above) demonstrate that the inventive combination of a wax dispersion and a cationic polymer protects the composition from color degradation, even under accelerated aging conditions.

The results described in the foregoing Examples demonstrate that the inventive stabilizing systems of the present invention not only provide physical stability by preventing visually perceivable phase separation, but also provide color stabilizing benefit.

Although several embodiments of the present invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A personal care composition comprising:
   a stability control system comprising
      a first component comprising a non-ionic opacifier comprising glyceryl oleate; and
      a second component comprising an ionic polymer;
   wherein the first and second component are present in a weight ratio ranging from about 8:1 to about 1:1.

2. The personal care composition according to claim 1, wherein the first and second component are present in a weight ratio ranging from about 6:1 to about 1:1.

3. The personal care composition according to claim 2, wherein the first and second component are present in a weight ratio ranging from about 4:1 to about 1:1.

4. The personal care composition according to claim 1, wherein the stability control system is present in an amount ranging from about 0.2 wt. % to about 4.0 wt. % based on the total weight of the personal care composition.

5. The personal care composition according to claim 4, wherein the stability control system is present in an amount ranging from about 0.275 wt. % to about 3.5 wt. % based on the total weight of the personal care composition.

6. The personal care composition according to claim 1, wherein the personal care composition is substantially free of styrene.

7. The personal care composition according to claim 1, wherein the non-ionic opacifier further comprises an ingredient selected from: glycol di-stearate, coco-glucoside, glyceryl stearate and a combination of two or more thereof.

8. The personal care composition according to claim 7, wherein the first component comprises glycol di-stearate, coco-glucoside, glyceryl oleate, and glyceryl stearate.

9. The personal care composition according to claim 1, wherein the non-ionic opacifier is present in an amount ranging from about 0.2 wt. % to about 2.5 wt. % based on the total weight of the personal care composition.

10. The personal care composition according to claim 9, wherein the non-ionic opacifier is present in an amount ranging from about 0.25 wt. % to about 2.1 wt. % based on the total weight of the personal care composition.

11. The personal care composition according to claim 1, wherein the first component has a pH ranging from about 3 to about 5.5.

12. The personal care composition according to claim 1, wherein the ionic polymer comprises a cationic polymer.

13. The personal care composition according to claim 12, wherein the cationic polymer comprises a copolymer of acrylamide and a diallyl dimethylammonium salt.

14. The personal care composition according to claim 13, wherein the diallyl dimethylammonium salt is diallyl dimethylammonium chloride.

15. The personal care composition according to claim 1, wherein the second component is present in an amount ranging from about 0.1 wt. % to about 1.5 wt. % based on the total weight of the personal care composition.

16. The personal care composition according to claim 1, wherein the personal care composition is separation stable at about 49° C. for at least four weeks.

17. The personal care composition according to claim 1, wherein the personal care composition is opaque.

18. The personal care composition according to claim 1, further comprising a base with a non-aqueous component that comprises at least one of benzoic acid, citric acid, fatty acid, glyceride, and polyalkylglycoside.

19. The personal care composition according to claim 1, further comprising water present in an amount ranging from about 65 wt. % to about 80 wt. % based on the total weight of the personal care composition.

20. The personal care composition according to claim 1, wherein the personal care composition is in a form selected from a body wash; a shower gel; and a liquid hand soap.

\* \* \* \* \*